US007163814B2

(12) United States Patent
Asako et al.

(10) Patent No.: US 7,163,814 B2
(45) Date of Patent: Jan. 16, 2007

(54) MODIFIED REDUCTASE AND ITS GENE, AND USE THEREOF

(75) Inventors: Hiroyuki Asako, Toyonaka (JP); Masatoshi Shimizu, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 438 days.

(21) Appl. No.: 10/608,625

(22) Filed: Jun. 30, 2003

(65) Prior Publication Data

US 2005/0191738 A1    Sep. 1, 2005

(30) Foreign Application Priority Data

Jul. 3, 2002   (JP) ............................. 2002-194344

(51) Int. Cl.
C12N 9/02 (2006.01)
C12N 15/00 (2006.01)
C12P 21/04 (2006.01)
C12Q 1/34 (2006.01)
C12Q 1/26 (2006.01)
C12Q 1/00 (2006.01)
C07H 21/04 (2006.01)
C12Q 1/68 (2006.01)

(52) U.S. Cl. .............................. 435/189; 435/4; 435/6; 435/18; 435/25; 435/440; 435/69.1; 435/71.1; 536/23.2; 536/23.7

(58) Field of Classification Search ................ 435/189, 435/440, 4, 6, 252.3, 320.1, 69.1, 71.1, 18, 435/25; 536/23.2, 23.7
See application file for complete search history.

(56) References Cited

U.S. PATENT DOCUMENTS

| | | | |
|---|---|---|---|
| 4,455,373 | A | 6/1984 | Higgins |
| 4,895,979 | A | 1/1990 | Noyori et al. |
| 5,908,953 | A | 6/1999 | Matsuda et al. |
| 6,218,156 | B1 | 4/2001 | Yasohara et al. |
| 6,312,933 | B1 | 11/2001 | Kimoto et al. |
| 2003/0134402 | A1 | 7/2003 | Asako et al. |
| 2003/0186400 | A1 | 10/2003 | Asako et al. |

FOREIGN PATENT DOCUMENTS

| | | |
|---|---|---|
| EP | 0 400 239 A1 | 12/1990 |
| EP | 0 501 353 A2 | 9/1992 |
| EP | 0 967 271 A1 | 12/1999 |
| EP | 1 013 758 A2 | 6/2000 |
| EP | 1 201 647 A2 | 5/2002 |
| EP | 1 213 354 A2 | 6/2002 |
| JP | 60-251890 A | 12/1985 |
| JP | 63-123387 A | 5/1988 |
| JP | 01-222787 A | 6/1989 |
| JP | 02-312593 A | 12/1990 |
| JP | 2532299 B2 | 6/1996 |
| JP | 2566962 B2 | 10/1996 |
| JP | 10-94399 A | 4/1998 |
| JP | 2001-294549 A | 10/2001 |

OTHER PUBLICATIONS

U.S. Appl. No. 10/608,533, filed Jun. 30, 2003, Asako et al.
U.S. Appl. No. 10/617,034, filed Jul. 6, 11, 2003, Itoh et al.
Itoh et al., "Chiral alcohol production by NADH-dependent phenylacetaldehyde reductase coupled with *in situ* regeneration of NADA," *Eur. J. Biochem.* 269, 2002, pp. 2394-2402.
Itoh et al., "Chirol alcohol production by β-ketoester reductase from *Penicillium citrinum* coupled with regeneration system of NADPH", *Journal of Molecular Catalysis B Enzymatic*, vol. 22, No. 3-4, Jun. 2, 2003, pp. 247-248.
Kometani et al., "Baker's Yeast Mediated Bioreduction. A New Procedure Using Ethanol as an Energ Source", *Chemistry Letters*, 1989, pp. 1465-1466.
Spiliotis et al., "Enhanced Optical Purity of 3-Hydroxyesters Obtained by Baker's Yeast Reduction of 3-Ketoesters", *Tetrahedron Letters*, vol. 31, No. 11, 1990, pp. 1615-1616.
Wei et al., "Baker's yeast mediated mono-reduction of 1,3-cyclohexanediones bearing two identical C(2) substituents", *Tetrahedron: Asymmetry*, vol. 12, 2001, pp. 229-233.
Itoh et al., "Production of chiral alcohols by enantioselective reduction with NADH-dependent phenylacetaldehyde reductase from *Corynebacterium* stain, ST-10", *Journal of Molecular Catalysis B: Enzymatic*, vol. 6, 1999, pp. 41-50.
Itoh et al., "Purification and Characterization of Phenylacetaldehyde Reductase from a Styrene-Assimilating *Corynebacterium* Strain, ST-10", *Applied and Environmental Microbiology*, vol. 63, No. 10, Oct. 1997, pp. 3783-3788.
Wang et al., "Cloning, sequence analysis, and expression in *Escherichia coli* of the gene encoding phenyklacetaldehyde reductase from styrene-assimilating *Corynebacterium* sp. Strain ST-10", *Applied Microbiology Biotechnology*, vol. 52, 1999, pp. 386-392.
Itoh et al., "1465. Chiral alcohols production by enantioselective reduction with NADH-dependent phenylacetaldehyde reductase (PAR)", *Book of Abstracts, 2000 International Chemical Congress of Pacific Basin Societies*, Dec. 14-19, 2000, p. 9.
Itoh et al., "3Y7p7. Production of optically active alcohol by using a phenylacetaldehyde reductase (PAR) recombinant strain", *Nippon Nogeikagaku Kaishi*, vol. 75, Mar. 5, 2001, with translation of 3Y7P7.
Itoh et al., "3F302β. Analysis of the phenylacetaldehyde reductase (PAR) gene from styrene-assimilating *Corynebacterium*", *Nippon Nogeikagaku Kaishi*, vol. 74, Mar. 5, 2000, with translation of 3F302β.

(Continued)

*Primary Examiner*—Tekchand Saidha
*Assistant Examiner*—Yong D. Pak

(57) ABSTRACT

There is provided a reductase characterized by
(i) an amino acid sequence of SEQ ID NO:1 having a substitution at amino acid position 54 or 104 or at both of the amino acid positions 54 and 104, or
(ii) an amino acid sequence defined in (a) having further deletion, substitution, or addition of an amino acid or acids and the like, which reductase is provided with good heat stability and selectivity.

5 Claims, No Drawings

OTHER PUBLICATIONS

Itoh et al., "3F303α. Production of optically active alcohol by using the phenylacetaldehyde reductase (PAR) from *Corynebhacterium* sp. ST10", *Nippon Nogeikagaku Kaishi*, vol. 74, Mar. 5, 2000, with translation of 3F303α.

Asako et al., "P214. Chiral Alcohol Production by β-Ketoester Reductase from *Penicillium citrinum* Coupled with Regeneration System of NADPH", *Chem. Litsy* 97, 6th International Symposium on Biocatalysis and Biotransformations, Jun. 28-Jul. 3, 2003, p. 489.

Lecture Summary Series of the 6th Organism Catalyst Chemistry Symposium, Dec. 12-13, 2002, p. 70, with partial English translation.

Conference Lecture Summary Series, published Mar. 5, 2003, 3A11a01, with partial English translation.

SEQUENCE LISTING

<160> NUMBER OF SEQ ID NOS: 31

<210> SEQ ID NO 1
<211> LENGTH: 325
<212> TYPE: PRT
<213> ORGANISM: Penicillium citrinum

<400> SEQUENCE: 1

Met Ser Asn Gly Lys Thr Phe Thr Leu Ser Asn Gly Val Lys Ile Pro
1               5                   10                  15

Gly Val Gly Phe Gly Thr Phe Ala Ser Glu Gly Ser Lys Gly Glu Thr
            20                  25                  30

Tyr Thr Ala Val Thr Thr Ala Leu Lys Thr Gly Tyr Arg His Leu Asp
        35                  40                  45

Cys Ala Trp Tyr Tyr Leu Asn Glu Gly Glu Val Gly Glu Gly Ile Arg
    50                  55                  60

Asp Phe Leu Lys Glu Asn Pro Ser Val Lys Arg Glu Asp Ile Phe Val
65                  70                  75                  80

Cys Thr Lys Val Trp Asn His Leu His Arg Tyr Glu Asp Val Leu Trp
                85                  90                  95

Ser Ile Asp Asp Ser Leu Lys Arg Leu Gly Leu Asp Tyr Val Asp Met
            100                 105                 110

Phe Leu Val His Trp Pro Ile Ala Ala Glu Lys Asn Gly Gln Gly Glu
        115                 120                 125

Pro Lys Ile Gly Pro Asp Gly Lys Tyr Val Ile Leu Lys Asp Leu Thr
    130                 135                 140

Glu Asn Pro Glu Pro Thr Trp Arg Ala Met Glu Lys Ile Tyr Glu Asp
145                 150                 155                 160

Arg Lys Ala Arg Ser Ile Gly Val Ser Asn Trp Thr Ile Ala Asp Leu
                165                 170                 175

Glu Lys Met Ser Lys Phe Ala Lys Val Met Pro His Ala Asn Gln Ile
            180                 185                 190

Glu Ile His Pro Phe Leu Pro Asn Glu Glu Leu Val Gln Tyr Cys Phe
        195                 200                 205

Ser Lys Asn Ile Met Pro Val Ala Tyr Ser Pro Leu Gly Ser Gln Asn
    210                 215                 220

Gln Val Pro Thr Thr Gly Glu Arg Val Ser Glu Asn Lys Thr Leu Asn
225                 230                 235                 240

Glu Ile Ala Glu Lys Gly Gly Asn Thr Leu Ala Gln Val Leu Ile Ala
                245                 250                 255

Trp Gly Leu Arg Arg Gly Tyr Val Val Leu Pro Lys Ser Ser Asn Pro
            260                 265                 270

Lys Arg Ile Glu Ser Asn Phe Lys Ser Ile Glu Leu Ser Asp Ala Asp
        275                 280                 285

Phe Glu Ala Ile Asn Ala Val Ala Lys Gly Arg His Phe Arg Phe Val
    290                 295                 300

Asn Met Lys Asp Thr Phe Gly Tyr Asp Val Trp Pro Glu Glu Thr Ala
305                 310                 315                 320

Lys Asn Leu Ser Ala
                325

<210> SEQ ID NO 2
<211> LENGTH: 978
<212> TYPE: DNA

```
<213> ORGANISM: Penicillium citrinum
<220> FEATURE:
<221> NAME/KEY: CDS
<222> LOCATION: (1)..(978)

<400> SEQUENCE: 2 atg tct aac gga aag act ttc aca ttg agc aac ggc gtc aag att cct       48
Met Ser Asn Gly Lys Thr Phe Thr Leu Ser Asn Gly Val Lys Ile Pro
 1               5                  10                  15 ggc gtc ggc ttt ggt acc ttc gct agt gaa ggt tcc aag ggc gag acc       96
Gly Val Gly Phe Gly Thr Phe Ala Ser Glu Gly Ser Lys Gly Glu Thr
             20                  25                  30 tat act gct gtc acc act gcc ctg aag acc ggt tac cgt cac ttg gac      144
Tyr Thr Ala Val Thr Thr Ala Leu Lys Thr Gly Tyr Arg His Leu Asp
         35                  40                  45 tgt gcc tgg tac tac ctg aac gag ggt gag gtt ggt gag ggt atc cgt      192
Cys Ala Trp Tyr Tyr Leu Asn Glu Gly Glu Val Gly Glu Gly Ile Arg
     50                  55                  60 gac ttc ctg aag gag aac ccc tcg gtg aag cgt gag gac atc ttc gtc      240
Asp Phe Leu Lys Glu Asn Pro Ser Val Lys Arg Glu Asp Ile Phe Val
 65                  70                  75                  80 tgc acc aag gtg tgg aac cac ctc cac cgt tat gag gac gtc ctc tgg      288
Cys Thr Lys Val Trp Asn His Leu His Arg Tyr Glu Asp Val Leu Trp
                 85                  90                  95 tcc att gac gac tcc ctg aag cgt ctt gga ctt gac tac gtt gat atg      336
Ser Ile Asp Asp Ser Leu Lys Arg Leu Gly Leu Asp Tyr Val Asp Met
            100                 105                 110 ttc ctc gtt cac tgg ccc att gct gcc gag aag aat ggc cag ggt gag      384
Phe Leu Val His Trp Pro Ile Ala Ala Glu Lys Asn Gly Gln Gly Glu
        115                 120                 125 ccc aag att ggc cct gac ggc aaa tac gtc att ctc aag gac ctg acc      432
Pro Lys Ile Gly Pro Asp Gly Lys Tyr Val Ile Leu Lys Asp Leu Thr
    130                 135                 140 gag aac ccc gag ccc aca tgg cgc gct atg gag aag att tat gag gat      480
Glu Asn Pro Glu Pro Thr Trp Arg Ala Met Glu Lys Ile Tyr Glu Asp
145                 150                 155                 160 cgc aag gcc agg tcc att ggt gtc tcc aac tgg acc att gcc gac ctt      528
Arg Lys Ala Arg Ser Ile Gly Val Ser Asn Trp Thr Ile Ala Asp Leu
                165                 170                 175 gag aag atg tcc aag ttc gcc aag gtc atg cct cac gcc aac cag atc      576
Glu Lys Met Ser Lys Phe Ala Lys Val Met Pro His Ala Asn Gln Ile
            180                 185                 190 gag att cac ccc ttc ctg ccc aac gag gag ctg gtg cag tac tgc ttc      624
Glu Ile His Pro Phe Leu Pro Asn Glu Glu Leu Val Gln Tyr Cys Phe
        195                 200                 205 tcc aag aac att atg ccc gtg gcc tac tct cct ctg ggc tcg cag aac      672
Ser Lys Asn Ile Met Pro Val Ala Tyr Ser Pro Leu Gly Ser Gln Asn
    210                 215                 220 cag gtt ccc acc acc ggt gag cgg gtc agc gag aac aag act ctg aac      720
Gln Val Pro Thr Thr Gly Glu Arg Val Ser Glu Asn Lys Thr Leu Asn
225                 230                 235                 240 gag atc gcc gag aag ggc ggc aac acc ctt gct cag gtt ctt att gcc      768
Glu Ile Ala Glu Lys Gly Gly Asn Thr Leu Ala Gln Val Leu Ile Ala
                245                 250                 255 tgg ggt ctg cgc cgt ggc tac gtc gtt ctc ccc aag agc tcc aac ccc      816
Trp Gly Leu Arg Arg Gly Tyr Val Val Leu Pro Lys Ser Ser Asn Pro
            260                 265                 270 aag cgc att gag tcc aac ttc aag agc att gag ctc tcc gat gcc gac      864
Lys Arg Ile Glu Ser Asn Phe Lys Ser Ile Glu Leu Ser Asp Ala Asp
        275                 280                 285
```

```
ttt gaa gcc atc aat gcc gtt gcc aag ggt cgt cac ttc cgt ttc gtc      912
Phe Glu Ala Ile Asn Ala Val Ala Lys Gly Arg His Phe Arg Phe Val
    290                 295                 300 aac atg aag gat act ttc gga tat gat gtc tgg ccc gag gag acc gcc      960
Asn Met Lys Asp Thr Phe Gly Tyr Asp Val Trp Pro Glu Glu Thr Ala
305                 310                 315                 320 aag aac ctg tct gcg tga                                              978
Lys Asn Leu Ser Ala
            325

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 3
gccatggcta tgtctaacgg aaagact                                         27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 4
cggatccgtt cacgcagaca ggttcttgg                                       29

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 5
tggtactacc agaacgaggg t                                               21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 6
ggctgaaaat cttctctcat                                                 20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 7
gactccctga agtgtcttgg a                                               21

<210> SEQ ID NO 8
```

```
<211> LENGTH: 27
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 8
gccatggcta tgtataaaga tttagaa                                          27

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 9
cggatccgtt atccgcgtcc tgc                                              23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 10
gagaggggcg gcaacaccct t                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 11
tccgacccca agcgcattga g                                                21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 12
tggtactacg gcaacgaggg t                                                21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 13
tggtactaca gcaacgaggg t                                                21

<210> SEQ ID NO 14
<211> LENGTH: 21
```

```
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 14
tggtactaca ccaacgaggg t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 15
tggtactact gcaacgaggg t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 16
tggtactact ataacgaggg t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 17
tggtactaca acaacgaggg t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 18
tggtactacg cgaacgaggg t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 19
tggtactacg tgaacgaggg t                                              21

<210> SEQ ID NO 20
<211> LENGTH: 21
<212> TYPE: DNA
```

<213> ORGANISM: Artificial Sequence
<220> FEATURE:
<223> OTHER INFORMATION: Description of Artificial Sequence: Designed
      oligonucleotide primer for PCR

<400> SEQUENCE: 20
tggtactaca ttaacgaggg t                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 21
tggtactaca tgaacgaggg t                                            21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 22
tggtactacc cgaacgaggg t                                            21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 23
tggtactaca aaaacgaggg t                                            21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 24
tggtactacc gcaacgaggg t                                            21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 25
tggtactacc ataacgaggg t                                            21

<210> SEQ ID NO 26
<211> LENGTH: 21
<212> TYPE: DNA
<213> ORGANISM: Artificial Sequence

```
<220> FEATURE:
<223> OTHER INFORMATION: Description of Artificial Sequence: Designed
      oligonucleotide primer for PCR

<400> SEQUENCE: 26
tggtactacg ataacgaggg t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 27
tggtactacg aaaacgaggg t                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 28
tgttgacaat taatcatccg                                                20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 29
aagcttgcat gccttcgggt cgac                                           24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 30
cggatccgag gaaacagacc atgg                                           24

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Designed
      oligonucleotide primer for PCR

<400> SEQUENCE: 31
ctctagagtt ataatttcgt agagattca                                      29
```

MODIFIED REDUCTASE AND ITS GENE, AND USE THEREOF

BACKGROUND OF THE INVENTION

1. Field of the Invention

The present invention relates to a modified reductase that can be used for reduction reaction, specifically reduction reaction of β-keto acid, and the like, and its gene and use thereof.

2. Background of the Invention

Reductases have been used recently for an organic synthesis reaction for production of compounds used as active ingredients of medicaments or agrochemicals or intermediates thereof, especially optically active compounds or intermediates thereof.

According to the present invention, there is provided a modified reductase having a wild-type amino acid sequence in which a certain amino acid has been substituted, which can produce reaction products with good optical purity.

The present invention provides:

(1) a reductase comprising
(i) an amino acid sequence of SEQ ID NO:1 having a substitution at amino acid position 54 or 104 or at both of the amino acid positions 54 and 104, or
(ii) an amino acid sequence defined in (i) having further deletion, substitution, or addition of an amino acid or acids, (hereinafter referred to as a reductase of the present invention);

(2) a reductase according to (1) above, which comprises
an amino acid sequence of SEQ ID NO:1 having
a substitution at amino acid position 54 or 104 or at both of the amino acid positions 54 and 104, and
further substitution of an amino acid or acids;

(3) a reductase according to (1) above, wherein said substitution is a single amino acid substitution at amino acid position 54;

(4) a reductase according to (1) above, wherein said substitution is a single amino acid substitution at amino acid position 104;

(5) a reductase according to (1) above, wherein amino acids at amino acid positions 54 and 104 are substituted by a same amino acid or different amino acids;

(6) a reductase according to (3) or (5) above, wherein the amino acid at amino acid position 54 is substituted by a non-aromatic amino acid;

(7) a reductase according to (3) or (5) above, wherein the amino acid at amino acid 54 is substituted by glutamine, glycine, serine, threonine, cysteine, asparagine, alanine, valine, isoleucine, methionine, lysine, arginine, aspartic acid, glutamic acid, tyrosine, proline or histidine;

(8) a reductase according to (4) or (5) above, wherein the amino acid at amino acid position 104 is substituted by cysteine;

(9) a reductase according to (1), (2), (3), (4) or (5), wherein said further substitution comprises a substitution at amino acid position 245 or 271 or at both of the amino acid positions 245 and 271;

(10) a reductase according to (9), wherein said further substitution comprises a single amino acid substitution at amino acid position 245 in the amino acid sequence of SEQ ID NO:1;

(11) a reductase according to (9) above, wherein said further substitution comprises a single amino acid substitution at amino acid position 271 in the amino acid sequence of SEQ ID NO:1;

(12) a reductase according to (9) or (10) above, wherein the amino acid at amino acid position 245 is substituted by arginine;

(13) a reductase according to (9) or (11) above, wherein the amino acid at amino acid position 271 is substituted by aspartic acid;

(14) a reductase according to (1) above, wherein
(a) the amino acid at amino acid position 54 is substituted by glutamine and the amino acid at amino acid position 104 is substituted by cysteine;
(b) the amino acid at amino acid position 54 is substituted by glutamine,
the amino acid of the position 104 is substituted by cysteine and said further substitution comprises substitution of the amino acid at amino acid position 271 by aspartic acid;
(c) the amino acid at amino acid position 54 is substituted by glutamine and
the amino acid at amino acid position 104 is substituted by cysteine, and
said further substitution comprises
the amino acid substitution at amino acid position 245 by arginine, and
the amino acid substitution at amino acid position 271 by aspartic acid;
(d) the amino acid of the position 54 is substituted by glutamine, and said further substitution comprises the amino acid substitution at amino acid position 245 by arginine;
(e) the amino acid of the position 54 is substituted by glutamine, and
said further substitution comprises
substitution of the amino acid at amino acid position 245 by arginine, and
substitution of the amino acid at amino acid position 271 by aspartic acid; or
(f) the amino acid at amino acid position 54 is substituted by glutamine and said further substitution comprises substitution of the amino acid at amino acid position 271 by aspartic acid;

(15) a polynucleotide comprising a nucleotide sequence that encodes the amino acid sequence of the reductase according to (1) or (8) above;

(16) a vector comprising the polynucleotide according to (15) above;

(17) a transformant comprising the polynucleotide according to (15) above or the vector according to (16) above;

(18) a vector according to (16) above, which further comprises a polynucleotide having a nucleotide sequence that encodes the amino acid sequence of a protein capable of converting NADP (an oxidation-type β-nicotineamide adeninedinucleotide phosphate) or NAD (an oxidation-type β-nicotineamide adeninedinucleotide) into NADPH or NADH (reduction-type);

(19) a transformant according to (17) above, which further comprises a polynucleotide having a nucleotide sequence that encodes the amino acid sequence of a protein capable of converting NADP (an oxidation-type β-nicotineamide adeninedinucleotide phosphate) or NAD (an oxidation-type β-nicotineamide adeninedinucleotide) into NADPH or NADH (reduction-type).

(20) a production method for $(S)_4$-halo-3-hydroxybutyrate ester, which comprises reacting 4-halo-3-oxobutyrate ester with the transformant according to (17) or (19) above or a treated material thereof;

(21) a method for modifying an enzyme, comprises substituting at least one single amino acid at amino acid positions 54 and 104 in the amino acid sequence of SEQ ID NO: 1, thereby selectivity of said enzyme is improved;

(22) a production method for a modified enzyme gene, which comprises replacing a codon that corresponds at least one of the amino acids at amino acid positions 54 and 104 of an amino acid sequence of SEQ ID NO: 1, with a codon that corresponds to the another amino acid(s), in a nucleotide sequence that encodes the amino acid sequence of SEQ ID NO: 1.

DETAILED DESCRIPTION OF THE INVENTION

Hereinafter the present invention is explained in more detail.

The present invention concerns a protein that comprises the sequence SEQ ID NO: 1 but has a substitution(s) at positions 54 and/or 104 of SEQ ID NO: 1. The region corresponding to SEQ ID NO: 1 in the protein may comprise further changes (deletions and/or substitutions and/or additions). Thus the protein will comprise a region which is homologous to SEQ ID NO: 1. Preferably proteins of the invention comprising such homologous regions will retain reductase activity.

The homologous sequence typically has at least 70% homology, preferably at least 80%, 90%. 95%. 97% or 99% homology, for example over a region of at least 30, 100, 200 or more contiguous amino acids, such as over the entire length of SEQ ID NO: 1. The homology may be calculated on the basis of amino acid identity (sometimes referred to as "hard homology").

For example the UWGCG Package provides the BEST-FIT program which can be used to calculate homology (for example used on its default settings) (Devereux el al (1984) *Nucleic Acids Research* 12. p387–395). The PILEUP and BLAST algorithms can be used to calculate homology or line up sequences (such as identifying equivalent or corresponding sequences (typically on their default settings)), for example as described in Altschul S. F. (1993) J Mol Evol 3 6:290–300: Altschul. S, F et al (1990). J Mol Biol 215: 403–10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the. sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs from SEQ ID NO:1 by less than 100 mutations, such as less than 70, less than 50, less than 30 or less than 15 mutations (each of which may be a substitution, deletion or addition of an amino acid).

The reductase having the amino acid sequence of SEQ ID NO:1 (hereinafter sometimes referred to as a wild-type reductase) is a reductase derived from *Penicillium citrinum* IF04631 strain (available from the Institute for Fermentation, Osaka (www.ifo.or.jp)). The activity of the reductase or the reductase of the present invention (i.e. ability to reduce a substrate) can be measured by, for example, mixing these reductase with, for example, methyl 4-bromo-3-oxobutyrate and NADPH, keeping the mixture at 30° C., and quantifying the amount of the liberated NADP+ using the absorbance of the reaction solution at 340 nm as an index.

In order to obtain a gene having a nucleotide sequence that encodes the amino acid sequence of the reductase of the present invention (hereinafter referred to as a gene of the present invention), a gene having a nucleotide sequence that encodes an amino acid sequence of the wild-type reductase (hereinafter referred to as a wild-type gene) is usually produced first. The wild-type gene is, for example, a gene having the nucleotide sequence of SEQ ID NO:2, and it can be obtained from *Penicillium citrinum* IF04631 strain according to a general procedure of gene engineering as described in, for example, J. Sambrook, E. F. Fritsch, T. Maniatis ed., Molecular Cloning 2nd Edition, Cold Spring Harbor Laboratory, 1989 and the like. That is, the reductase gene of the present invention is prepared by preparing a cDNA library according to a method described in "New Cell Technology Experimental Protocol" (Division of Oncology, Institute of Medical Science, University of Tokyo ed. Shujunsha Co., Ltd, 1993) from *Penicillium citrinum* IF04631 strain and conducting PCR using the prepared cDNA library as a template and a suitable primer to amplify a DNA comprising a nucleotide sequence that encodes the amino acid sequence of SEQ ID NO:1, a DNA comprising a nucleotide sequence that encodes an amino acid sequence in which one or more of amino acid(s) of the amino acid sequence of SEQ ID NO:1 has (have) been deleted, replaced or added, or a DNA having the nucleotide sequence of SEQ ID NO:2 and the like.

When PCR is conducted using the cDNA library derived from *Penicillium citrinum* and using an oligonucleotide having the nucleotide sequence of SEQ ID NO:3 and an oligonucleotide having the nucleotide sequence of SEQ ID NO:4 as primers, the reductase gene is prepared by amplifying the DNA consisting of the nucleotide sequence of SEQ ID NO:2.

The reductase of the present invention comprises (i) an amino acid sequence of SEQ ID NO:1 having a substitution of an amino acid at amino acid position 54 or 104 or at both of the amino acid positions 54 and 104, or (ii) an amino acid sequence defined in (a) having further deletion, substitution, or addition of an amino acid or acids.

Said deletion, substitution, or addition of an amino acid or acids in the amino acid sequence of (ii) above typically means deletion, substitution, or addition of up to several amino acids and is conservative (i.e., equivalent sequence). Preferred is substitution.

For example, the "substitution" typically means the substitution of an amino acid of the wild-type reductase with another amino acid having similar characteristics with respect to hydrophobicity, electron charge, pK, characteristic of the steric structure and the like, and such substitution includes substitution of amino acids within the respective group of (1) glycine, and alanine; (2) valine, isoleucine, and leucine; (3) aspartic acid, glutamic acid, asparagine, and glutamine; (4) serine, and threonine; (5) lysine, and arginine; or (6) phenylalanine, and tyrosine.

The gene of the present invention can be prepared by introducing site-specific mutation in the wild-type gene. The methods for introducing site-specific mutation include methods by, for example, Olfert Landt et al. (Gene 96 125–128 1990), Smith et al. (Genetic Engineering 3 1 Setlow, J. and Hollaender, A Plenum: New York), Vlasuk et al. (Experimental Manipulation of Gene Expression, Inouye, M.: Academic Press, New York), Hos. N. Hunt et al. (Gene 77 51 1989), or utilization of commercially available kit including Mutan-Express Km (manufactured by Takara Shuzo Co., Ltd.), TaKaRa La PCR in vitro Mutagenesis Kit (manufactured by Takara Shuzo Co., Ltd.), and the like.

For example, in order to prepare the gene of the present invention that encodes the amino acid sequence of SEQ ID NO:1 in which the amino acid at amino acid position 54 has been replaced with another amino acid using the method by Olfert Landt et al. (Gene 96 125–128 1990), the vector DNA comprising the wild-type gene having the nucleotide sequence of SEQ ID NO:2 is prepared first, for example, according to the methods described in J. Sambrook, E. F. Fritsch, T. Maniatis ed.; Molecular Cloning 2nd edition, Cold Spring Harbor Laboratory, 1989 and the like. Then the DNA fragment may be amplified by PCR method using the obtained vector DNA as a template, for example, using an oligonucleotide comprising a nucleotide sequence that encodes the amino acid sequence of SEQ ID NO:1 in which the amino acid of the position 54 has been substituted by another amino acid (e.g., an oligonucleotide having the nucleotide sequence of SEQ ID NO:5) as one primer and an oligonucleotide having the nucleotide sequence of SEQ ID NO:6 as the other primer. The condition of the PCR comprises, for example, repeating a cycle comprising keeping at 94° C. for 5 min, then keeping at 94° C. for 1 min, then at 50° C. for 2 min and at 75° C. for 3 min, for 20 times, and keeping at 75° C. for 8 min. The thus-amplified DNA fragments may be amplified by PCR method, after purification as well as addition of the vector DNA comprising the wild-type gene having the nucleotide sequence of SEQ ID NO:2 and an oligonucleotide primer having the nucleotide sequence of SEQ ID NO:3. The thus-obtained DNA fragments may be digested with, for example, restriction endonucleases NcoI and XbaI, and ligated with the vector DNA comprising the wild-type reductase gene that have been similarly digested with restriction endonuclease, to give the objective gene of the present invention.

Another amino acid that may substitute the amino acid of the position 54 includes, for example, glutamine, glycine, serine, threonine, cysteine, asparagine, alanine, valine, isoleucine, methionine, lysine, arginine, aspartic acid, glutamic acid, tyrosine, proline, histidine and the like, preferred is a non-aromatic amino acid such as glutamine, glycine, serine, threonine, cysteine, asparagine, alanine, valine, isoleucine, methionine, lysine, arginine, aspartic acid, glutamic acid, proline or the like.

Furthermore, for example, in order to prepare the gene of the present invention that encodes the amino acid sequence of SEQ ID NO:1 in which the amino acid of the position 104 has been substituted by another amino acid using the method by Olfert Landt et al. (Gene 96 125–128 1990), the vector DNA comprising the wild-type gene having the nucleotide sequence of SEQ ID NO:2 is prepared first, for example, according to the methods described in J. Sambrook, E. F. Fritsch, T. Maniatis ed.; Molecular Cloning 2nd edition, Cold Spring Harbor Laboratory, 1989 and the like. Then the DNA fragment may be amplified by PCR method, using the obtained vector DNA as a template, for example, using an oligonucleotide comprising a nucleotide sequence that encodes the amino acid sequence of SEQ ID NO:1 in which the amino acid of the position 104 has been substituted by another amino acid (e.g., an oligonucleotide having the nucleotide sequence of SEQ ID NO:7) as one primer and an oligonucleotide having the nucleotide sequence of SEQ ID NO:6 as the other primer. The condition of the PCR comprises, for example, repeating a cycle comprising keeping at 94° C. for 5 min, then keeping at 94° C. for 1 min, at 50° C. for 2 min and at 75° C. for 3 min, for 20 times, and keeping at 75° C. for 8 min. The thus-amplified DNA fragments may be amplified by PCR method, after purification as well as addition of the vector DNA comprising the wild-type gene having the nucleotide sequence of SEQ ID NO:3 and an oligonucleotide primer having the nucleotide sequence of SEQ ID NO:4. The thus-obtained DNA fragments may be digested with, for example, restriction endonuclease NcoI and XbaI, and ligated with the vector DNA comprising the wild-type gene that have been digested with restriction endonuclease, to obtain the gene of the present invention.

The amino acid that may substitute the amino acid at amino acid position 104 includes, for example, cysteine and the like.

Of course, both the of the amino acids at amino acid positions 54 and 104 of the amino acid sequence of SEQ ID NO:1 may be independently substituted, for example with a same amino acid or different amino acids.

The specific examples of the gene of the present invention include, a gene that encodes:

(a) an reductase having an amino acid sequence of SEQ ID NO:1 having amino acid substitutions of the amino acid at position 54 of the amino acid sequence of SEQ ID NO:1 with glutamine, and the amino acid at the position 104 of the amino acid sequence of SEQ ID NO:1 with cysteine;

(a1) a reductase having an amino acid sequence of SEQ ID NO:1 having an amino acid substitution of the amino acid of the position 54 of the amino acid sequence of SEQ ID NO:1 with glutamine;

(a2) a reductase having an amino acid sequence of SEQ ID NO:1 having a substitution of an amino acid at amino acid position 104 of the amino acid sequence of SEQ ID NO:1 with cysteine, or the like.

The present reductase may comprise a further substitution of an amino acid at amino acid position 245 or 271 or at both of the amino acid positions 245 and 271 of the amino acid sequence of SEQ ID NO:1.

Examples thereof include, for example, a reductase comprising
an amino acid sequence of SEQ ID NO:1 having
a substitution at amino acid position 54 or 104 or at both of the amino acid positions 54 and 104, and further substitution at amino acid position 245 or 271 or at both of the amino acid positions 245 and 271 in the amino acid sequence of SEQ ID NO:1, which may be referred to as a further modified gene.

For example, a polynucleotide that encodes the amino acid sequence of the reductase above of the present invention may be prepared as previous described, for example, by the method of Olfert Landt et al. (Gene 96 125–128 1990) and the like.

Examples of the amino acid that may substitute the amino acid at amino acid position 245 include, for example, arginine and the like, and examples of the amino acid that may substitute the amino acid at amino acid position 271 include, for example, aspartic acid and the like.

The specific examples of the gene of the present invention include a gene encoding an amino acid sequence of SEQ ID NO:1 in which:

(a) the amino acid at amino acid position 54 of the amino acid sequence of SEQ ID NO:1 is substituted by glutamine, and
the amino acid at amino acid position 104 of amino acid sequence of SEQ ID NO:1 is substituted by cysteine;

(b) the amino acid at amino acid position 54 of the amino acid sequence of SEQ ID NO:1 is substituted by glutamine,
the amino acid at amino acid the position 104 of the amino acid sequence of SEQ ID NO:1 is substituted by cysteine, and
the amino acid at amino acid position 271 of the amino acid sequence of SEQ ID NO:1 is substituted by aspartic acid;

(c) the amino acid at amino acid position 54 of the amino acid sequence of SEQ ID NO:1 is substituted by glutamine,
the amino acid at amino acid position 104 of the amino acid sequence of SEQ ID NO:1 is substituted by cysteine,
the amino acid at amino acid the position 245 of the amino acid sequence of SEQ ID NO:1 is substituted by arginine, and
the amino acid at amino acid position 271 of the amino acid sequence of SEQ ID NO:1 is substituted by aspartic acid;

(d) the amino acid of the position 54 of the amino acid sequence of SEQ ID NO:1 is substituted by glutamine, and the amino acid of the position 245 of the amino acid sequence of SEQ ID NO:1 is substituted by arginine;

(e) the amino acid of the position 54 of the amino acid sequence of SEQ ID NO:1 is substituted by glutamine,
the amino acid of the position 245 of the amino acid sequence of SEQ ID NO:1 is substituted by arginine,
and the amino acid of the position 271 of the amino acid sequence of SEQ ID NO:1 is substituted by aspartic acid; or (f) the amino acid of the position 54 of the amino acid sequence of SEQ ID NO:1 is substituted by glutamine, and the amino acid of the position 271 of the amino acid sequence of SEQ ID NO:1 is substituted by aspartic acid, and the like.

Using the thus-prepared gene of the present invention or the second gene of the present invention, the reductase of the present invention or the second reductase of the present invention can be produced in a large amount and obtained according to a general method of gene engineering. Specifically, a transformant is prepared by, for example, preparing a vector that can express the gene of the present invention in a host cell of a microorganism and the like, and introducing the vector into a host cell and transforming the host cell. Then the transformed microorganism prepared as above may be cultivated according to a general cultivation method.

The above-mentioned vector can be constructed by introducing a vector that can be used in a host cell to which the gene of the present invention or the second gene of the present invention is introduced (hereinafter referred to as a basic vector), for example, a vector which comprises gene information capable of replicating in a host cell and can proliferate independently, can be isolated and purified from the host cell, and has a detectable marker, into the host cell, according to a general method of gene engineering.

As used herein, the "basic vector" specifically includes, when E. coli is used as a host cell, such as vector pUC119 (manufactured by Takara Shuzo Co., Ltd.), phagemid pBluescript II (manufactured by Stratagene) and the like. When a bud yeast is used as a host cell, the basic vector includes vectors pGBT9, pGAD424, pACT2 and the like (manufactured by Clontech, Inc.). When a mammalian cell is used as a host cell, the basic vector includes vectors such as pRc/RSV, pRc/CMV (manufactured by Invitrogen Corporation) and the like, a vector comprising an autonomously replicating origin derived from viruses such as bovine papilloma virus vector pBPV (manufactured by Amarsham Pharmacia Biotech, Corp.) or EB virus vector pCEP4 (manufactured by Invitrogen Corporation) and the like, viruses such as vaccinia virus and the like. Furthermore, when an insect cell is used as a host cell, the basic vector includes an insect virus such as baculo virus and the like.

When the vector of the present invention is constructed with the vector comprising an autonomously replicating origin, such as the above-mentioned vector pACT2 for yeast, bovine papilloma virus vector pBPV, EB virus vector pCEP4 and the like, said vector is retained in a host cell as an episome when it is introduced in said cell.

The vector of the present invention may further comprise a polynucleotide having a nucleotide sequence that encodes the amino acid sequence of a protein capable of converting an oxidation-type β-nicotineamide adeninedinucleotide phosphate or an oxidation-type β-nicotineamide adeninedinucleotide into reduction-type. By using such vector of the present invention, a transformant of the present invention further comprising a polynucleotide having a nucleotide sequence that encodes the amino acid sequence of a protein capable of converting an oxidation-type β-nicotineamide adeninedinucleotide phosphate or an oxidation-type β-nicotineamide adeninedinucleotide into reduction-type can be prepared.

The vector of the present invention capable of expressing the gene of the present invention or the second gene of the present invention in a host cell can be constructed by, binding a promoter capable of functioning in a host cell to the upper stream of the gene of the present invention or the second gene of the present invention in functionable manner, and incorporating the gene in the above-mentioned basic vector. As used herein, "binding in functionable manner" means binding a promoter with the gene of the present invention or the second gene of the present invention in a manner that the gene of the present invention or the second gene of the present invention is expressed in the host cell to which the gene of the present invention is introduced under the control of said promoter. The promoter capable of functioning in a host cell may include DNA that shows promoter activity in a host cell to which the promoter is introduced. For example, when the host cell is E. coli, the promoter includes a promoter of E. coli, lactose operon (lacP), a promoter of tryptophan operon (trpP), a promoter of arginine operon (argP), a promoter of galactose operon (galP), tac promoter, T7 promoter, T3 promoter, λ phage promoter (λ-pL, λ-pR) and the like. When the host cell is an animal cell or fission yeast, the promoter includes Rous sarcoma virus (RSV) promoter, cytomegalovirus (CMV) promoter, an early or late promoter of simian virus (SV40), mouse mammary tumor virus (MMTV) promoter and the like. When the host cell is bud yeast, the promoter includes ADH1 promoter and the like, which can be prepared from a yeast expression vector pAAH5 comprising the ADH1 promoter and ADH1 terminator [available from Washington Research Foundation, Ammerer et al., Method in Enzymology, 101 part (p.192–201)] according to a general method of gene engineering. The ADH1 promoter is included in the U.S. patent application No. 299,733 assigned to the Washington Research Foundation, and when the promoter is used for industrial or commercial purpose, permission by the Assignee will be required.

When a basic vector that previously comprises a promoter that functions in a host cell is used, the gene of the present invention or the second gene of the present invention may be inserted in the downstream of the promoter so that the promoter binds with the gene of the present invention or the second gene of the present invention in functionable form. For example, the above-mentioned vectors pRc/RSV, pRc/CMV and the like each contains a cloning site in the downstream of the promoter capable of functioning in an animal cell. By introducing the vector, which has been obtained by inserting the gene of the present invention in the cloning site, into an animal cell, the gene of the present invention can be expressed in the animal cell. Since these vectors previously include an autonomously replicating origin of SV40 (ori), when the vectors are introduced in a cultivated cell that has been transformed with an ori-deleted SV40 genome (e.g., COS cell and the like), the copy number of the vector in a cell is remarkably increased, which can result in the expression of the gene of the present invention, which has been incorporated in the vector, in a large amount. Furthermore, the above-mentioned vector pATC2 for yeast has an ADH1 promoter, and when the gene of the present invention is inserted in the lower stream of the ADH1 promoter of said vector or a derivative thereof, the vector of the present invention that can express the gene of the present invention in a large amount in a bud yeast such as CG1945 (manufactured by Clontech, Inc.) and the like, can be constructed.

As the host cell, for example, when it is a microorganism, both eukaryote and prokaryote can be used, and the cell includes *E. coli* and the like. The above-mentioned vector of the present invention can be introduced in the host cell according to a method usually employed of gene engineering to transform the host cell.

As a method for introducing the vector of the present invention into a host cell, a general method for introduction depending on the kind of the host cell can be used. For example, when *E. coli* is used as a host cell, general methods such as calcium chloride method, electroporation method and the like as described in J. Sambrook, E. F. Fritsch, T. Maniatis ed., Molecular Cloning 2nd Edition, Cold Spring Harbor Laboratory, 1989 and the like can be used. On the other hand, when a mammalian cell or insect cell is used as a host cell, the vector can be introduced according to general transgenic method such as calcium phosphate method, DEAE dextran method, electroporation method, lipofection method and the like. When yeast is used as a host cell, the introduction can be carried out using such as Yeast transformation kit (manufactured by Clontech, Inc.) based on lithium method, and the like.

When a virus is used as a vector, the genome of the virus can be introduced in a host cell according to the above-mentioned general transgenic method, or by infecting the host cell with virus particles comprising the genome of the virus in which the gene of the present invention has been inserted.

In order to screen the transformant of the present invention, for example, the host cell to which the vector of the present invention and a marker gene have been introduced may be cultivated according to various methods depending on the characteristic of the marker gene. For example, when the marker gene is a gene that provides drug tolerance for a screening agent having lethal activity for the host cell, the host cell to which the vector of a present invention have been introduced may be cultivated using a culture comprising the screening agent. The combination of a gene that provides drug tolerance and a screening agent includes the combination of a gene that provides neomycin-resistance with neomycin, a gene that provides hygromycin-resistance and hygromycin, a gene that provides blasticidin S-resistance with blasticidin S, and the like. Furthermore, when the marker gene is a gene that complements the auxotrophy of the host cell, the cell to which the vector of the present invention have been introduced may be cultivated using a minimal medium that does not contain nutrients corresponding to the auxotrophy. When the vector of the present invention capable of expressing the gene of the present invention or the second gene of the present invention in a host cell is introduced, a detection method based on the enzyme activity of the reductase of the present invention or the second reductase of the present invention may be used.

In order to obtain the transformant of the present invention in which the gene of the present invention is located in a chromosome of a host cell, for example, the vector of the present invention and a vector having a marker gene are firstly digested with a restriction endonuclease and like to be formed in linear shape, and are then introduced in a host cell according to the above-mentioned method. The cell is then cultivated, generally for several weeks, and the objective transformant is screened and obtained based on the expression amount of the introduced marker gene. Alternatively, the transformant of the present invention which the gene of the present invention or the second gene of the present invention has been introduced in a chromosome of a host cell can be screened and obtained by, for example, introducing firstly the vector of the present invention having a gene that provides screening agent, as a marker gene, in a host cell, passage cultivating the cell in a medium containing a screening agent for not less than several weeks, and purification culturing the screening drug-resistant clone that has been colonially survived. In order to confirm that the gene of the present invention or the second gene of the present invention has been included in the chromosome of the host cell, the existence of the gene of the present invention or the second gene of the present invention may be detected by, preparing the genomic DNA of said cell according to a general method of gene engineering, and subjecting the thus-prepared DNA to a method such as PCR in which the DNA having the partial nucleotide sequence of the gene of the present invention or the second gene of the present invention is used as a primer or a probe, Southern hybridization and the like. Since the transformant can be preserved by cryo preservation and if required, can be defrosted before use, it can save the labor of preparation of tranformant in each experiment, and a test can be carried out using the transformant in which its characteristic or handling condition have been confirmed.

The thus-obtained transformant comprising a vector comprising the gene of the present invention or the second gene of the present invention (hereinafter sometimes referred to as the transformant of the present invention) can be cultivated according to a general method of cell cultivation.

For example, when the transformant of the present invention is a microorganism, the transformant can be cultivated using various media that suitably includes carbon source, nitrogen source, organic or inorganic salts and the like, which are used in general cultivation of general microorganisms. For example, the carbon source includes sugars such as glucose, fructose, sucrose, dextrin and the like, sugar alcohols such as glycerol, sorbitol and the like, organic acids such as fumaric acid, citric acid and the like. The amount of the carbon source to be added to the medium may be generally about 0.1 to 10%. The nitrogen source includes ammonium salts of inorganic acid such as ammonium chloride, ammonium sulfate, ammonium phosphate and the like, ammonium salts of organic acid such as ammonium fumarate, ammonium citrate and the like, natural organic nitrogen sources such as meat extract, yeast extract, malt extract, soybean powder, corn steep liquor, cottonseed powder, dried yeast, casein hydrolysate and the like, amino acids and the like. Among these, many of the organic nitrogen sources can be used in combination with the carbon sources. The amount of the nitrogen source to be added to the medium may be generally about 0.1 to 10%. The inorganic salt includes such as alkaline metal phosphate such as potassium phosphate, sodium phosphate and the like, alkaline metal chloride such as potassium chloride, sodium chloride and the like, metal sulfate such as magnesium sulfate, ferrous sulfate and the like. The amount of the inorganic salt to be added to the medium is generally about 0.001 to 1%.

Additionally, the ability of the transformant of the present invention can be enhanced by previously adding a small amount of substrate, which is raw material, to a medium. The amount of the substrate to be added is generally about not less than 0.001%, preferably 0.1 to 1%.

The cultivation is conducted according to a general method for general microorganisms, and solid cultivation, liquid cultivation (revolving-type shaking cultivation, reciprocating-type shaking cultivation, jar fermenter cultivation, tank cultivation and the like) and the like may be used. Specifically, when a jar fermenter is used, introduction of sterilized air is necessary, and the condition for purging being used is about 0.1 to about 2 times/min of the amount of the cultivation solution. The temperature for cultivation and the pH of the medium can be suitably selected from the range in which the microorganism grows, and for example, the cultivation under the cultivation temperature of about 15° C. to about 40° C. and in a medium having the pH of about 6 to about 8 is preferred. While the period for cultivation varies depending on various conditions for cultivation, about one day to about five days is generally desired. When an expression vector having an inducible promoter such as temperature-shift type, IPTG inducible type and the like is used, the induction period is preferably within one day, generally several hours.

Alternatively, when the transformant is an animal cell such as mammalian cell, insect cell and the like, the transformant can be cultivated using media that are used in general cultivation of general microorganisms. When the transformant is prepared using a screening agent, it is preferable to cultivate the transformant in the presence of the screening agent. In the case of mammalian cell, it may be cultivated using a DMEM medium (manufactured by Nissui Co,. Ltd. and the like) in which FBS has been added so that the final concentration is adjusted to 10%, at 37° C. and in the presence of 5% $CO_2$, with changing the cultivation solution every several days. When the cells have been proliferated and become confluent, for example, PBS solution in which trypsin has been added so that the concentration is adjusted to about 0.25 (w/v), is added thereto to disperse the cells, the solution is diluted by several folds and inoculated to a new dish, and the cultivation is continued. In the case of insect cell, similarly, for example, the cell may be cultivated at the cultivation temperature of 25° C. to 35° C. using a cultivation solution for insect cell, such as Grace's medium comprising 10% (v/v) PBS and 2% (w/v) Yeastlate, and the like. During the cultivation, when the cell is easy to exfoliate from the dish, such as Sf21 cell and the like, passage cultivation may be carried out without using trypsin solution and with dispersing by pipetting. When a transformant comprising a virus vector of baculovirus and the like is used, the cultivation is preferably finished until the cytoplasmic effect is expressed and the cells are killed, for example, up to 72 hours after the infection with the virus.

The thus-prepared transformant of the present invention that produces the reductase of the present invention or the second reductase of the present invention or a treated transformant can be used for an organic synthesis reaction for production of compounds used as active ingredients of medicaments or agrochemicals (for example, 4-halo-3-oxobutyrate ester) or intermediates thereof, especially optically active compounds or intermediates thereof, as a bioreactor that reduces a substrate.

The treated substance of the transformant of the present invention includes the cultivated transformant of the present invention that has been obtained by cultivating as above, for example, the transformant of the present invention itself, a cultivation solution containing the transformant of the present invention, or a treated transformant such as an insoluble transformant in which sterilized cells that have been sterilized by physical sterilization (heating, drying, freezing, ray, ultrasonic, filtration, electrization) or chemical sterilization (alkaline, acid, halogen, oxidizing agent, sulfur, boron, arsenic, metal, alcohol, phenol, amine, sulfide, ether, aldehyde, ketone, cyanogen, antibiotic) and the like, lyophilized cells, acetone-dried cells, crushed cells, autolyzed cell, cells treated with ultrasonic, cell extract, crude purified enzyme, purified enzyme, or treated transformant, has been immobilized by a known method such as polyacrylic amide method, sulfur-containing polysacchalide method (for example, carrageenan gel method), arginic acid gel method, agar gel method and the like.

As mentioned above, the reductase of the present invention or the second reductase of the present invention is collected and purified from the cultivated transformant that has been obtained by cultivating the transformant of the present invention, and which can be used as an enzyme reactor. The collection and purification of the reductase from the cultivated transformant of the present invention can be carried out by suitably combining general methods for extraction, isolation and purification for protein. For example, the collection and purification of the reductase of the present invention may be carried out by, for example, collecting the cultivated transformant of the present invention by centrifugation and the like after cultivation is completed, crushing or bacteriolysing, and using various chromatography methods such as ion exchange, hydrophobic, gel permeation and the like. Furthermore, as mentioned above, the transformant of the present invention, the reductase of the present invention or the second reductase of the present invention may be immobilized onto a suitable carrier, and which can be used as a reactor.

By reacting the transformant of the present invention or a treated material thereof with 4-halo-3-oxobutyrate ester, for example, (S)-4-halo-3-hydroxybutyrate ester can be prepared.

The above-mentioned 4-halo-3-oxobutyrate ester is an ester of formula 1:

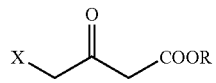

wherein X is chlorine atom, bromine atom or iodine atom, and R is an alkyl group, an substituted or unsubstituted aryl group. The alkyl group represented by R in the ester of formula 1 is preferably a lower alkyl group having 1 to 8 carbon atom(s).

Specifically, the ester includes methyl 4-chloro-3-oxobutyrate, ethyl 4-chloro-3-oxobutyrate, propyl 4-chloro-3-oxobutyrate, methyl 4-bromo-3-oxobutyrate, ethyl 4-bromo-3-oxobutyrate, propyl 4-bromo-3-oxobutyrate, octyl 4-bromo-3-oxobutyrate and the like.

The reaction is generally carried out in the presence of water and reduction-type nicotineamide adeninedinucleotide phosphate (hereinafter referred to as NADPH). The water used in the reaction may be an aqueous buffer solution. The buffering agent used for the aqueous buffer solution includes alkaline metal phosphates such as sodium phosphate, potassium phosphate and the like, alkaline metal acetates such as sodium acetate solution, potassium acetate and the like, or a mixture thereof.

During the above-mentioned reaction, an organic solvent may exist besides water. The organic solvent that may exist includes ethers such as t-butyl methyl ether, diisopropyl ether, tetrahydrofuran and the like, esters such as ethyl formate, ethyl acetate, propyl acetate, butyl acetate, ethyl propionate, butyl propionate and the like, hydrocarbons such as toluene, hexane, cyclohexane, heptane, isooctane and the like, alcohols such as methanol, ethanol, 2-propanol, butanol, t-butyl alcohol and the like, organic sulfur compounds such as dimethyl sulfoxide and the like, ketones such as acetone and the like, nitriles such as acetonitrile and the like, or a mixture thereof.

The reaction in the above-mentioned method is carried out by, for example, mixing water, NADPH and 4-halo-3-oxobutyrate ester with the transformant of the present invention or a treated transformant, optionally in the presence of an organic solvent and the like, by stirring, shaking and the like.

While the pH for the reaction in the above-mentioned method can be suitably selected, the pH is generally 3 to 10. While the temperature for the reaction can be suitably selected, the temperature is generally in the range of 0 to 60° C., in view of stability of raw materials and products and reaction velocity.

The progress of the reaction can be monitored by, for example, tracing the amount of 4-halo-3-oxobutyrate ester in the reaction solution using liquid chromatography and the like. While the reaction time can be suitably selected, the time is generally in the range of 0.5 hr to 10 days.

The collection of the (S)-4-halo-3-hydroxybutyrate ester from the reaction solution may be carried out by any of the generally known methods.

For example, purification method by conducting a post-treatment such as extraction of the reaction solution with an organic solvent, concentration and the like, optionally in combination with column chromatography, distillation and the like, is exemplified. The present invention also relates to: a method for modifying an enzyme, characterized in that the method comprises replacing at least one of the amino acid residues 54 and 104 in the amino acid sequence of SEQ ID NO:1, with the another amino acid(s), so as to improve the optical purity of the reaction product or cognition of said enzyme to the absolute configuration of a substrate in the reduction reaction in which said enzyme functions as a catalyst; and a production method for a modified enzyme gene, characterized in that the method comprises replacing a codon of at least one of the amino acid residues 54 and 104 of an amino acid sequence of SEQ ID NO:1, with a codon of another amino acid(s), in the nucleotide sequence encoding the amino acid sequence of SEQ ID NO:1.

EXAMPLES

Hereinafter the present invention is explained in more detail with referring to the Preparation Examples and the like, which do not limit the present invention.

Example 1

Preparation of a Gene of a Wild-type Reductase, which is a Template DNA (1-1) Preparation of a cDNA Library A medium (a solution of potato dextrose broth (manufactured by Becton Dickinson and Company) in water, 24 g/L) (100 ml) was put into a 500 ml flask and sterilized at 121° C. for 15 min. The thus-prepared medium was inoculated with a cultivation solution of *Penicillium citrinum* IFO4631 strain (available from the Institute for Fermentation, Osaka (www.ifo.or.jp), which solution had been previously cultivated in a liquid culture having the above-mentioned composition (30° C., 48 hr, cultivated with shaking) (0.5 ml), and cultivated at 30° C. for 72 hr with shaking.

After cultivation, the obtained cultivation solution was centrifuged (8000×g, 10 min) to collect bacterial cells as precipitate. The collected bacterial cells were washed three times with 20 mM monopotassium phosphate-dipotassium phosphate buffer (pH 7.0) (50 ml) to give wet bacterial cells (about 1.0 g).

The whole RNA was prepared from the thus-obtained wet bacterial cells using guanidium thiocyanate-phenol-chloroform method. An RNA having poly (A) was obtained from the thus-prepared whole RNA using Oligotex (dT) 30-Super (manufactured by Takara Shuzo Co., Ltd.)

The cDNA library was prepared according to the Gubler and Hoffman method. Firstl, a single-stranded cDNA was prepared using the thus-obtained RNA having poly (A), Oligo (dT) 18-linker primer (XhoI-containing site, manufactured by Takara Shuzo Co., Ltd.), RAV-2 Rtase and Super Script II Rtase. To the prepared single-stranded cDNA (the reaction solution containing the cDNA) were added *E. coli*

DNA polymerase, *E. coli* Rnase/*E. coli* DNA Ligase Mixture and T4 DNA Polymerase to synthesize a double-stranded cDNA, which was then subjected to blunt-ending.

The thus-obtained double-stranded cDNA and an EcoRI-NotI-BamHI adaptor (manufactured by Takara Shuzo Co., Ltd.) were subjected to ligation. The DNA obtained by the ligation was subjected to phosphorylation treatment, cleavage treatment with XhoI, and treatment for removing low molecular weight DNA with a spin column (manufactured by Takara Shuzo Co., Ltd.), and ligated with λ ZapII (cleavage of EcoRI-XhoI) and packaged using an in vitro packaging kit (manufactured by STRATAGENE Corporation) to prepare a cDNA library (hereinafter also referred to as cDNA library (A)).

(1-2) Preparation of a Vector Comprising a Wild-type Reductase Gene (Construction of Vector pTrcRPc)

PCR was carried out using an oligonucleotide having the nucleotide sequence of SEQ ID NO:3 (including NcoI) and an oligonucleotide having the nucleotide sequence of SEQ ID NO:4 (including BamHI) as primers, and using the cDNA library prepared in the above-mentioned (1-1) as a template, at the following composition of the reaction solution and reaction condition (using the Expand High Fidelity PCR system, manufactured by Roche Diagnostic Systems Inc.).

Composition of the Reaction Solution

| cDNA library stock solution | 1 μl |
|---|---|
| dNTP (each 2.5 mM-mix) | 0.4 μl |
| Primer (20 pmol/μl) | Each 0.75 μl |
| 10x buffer (with MgCl$_2$) | 5 μl |
| enz. expand HiFi (3.5 × 10$^3$ U/ml) | 0.375 μl |
| Ultrapure water | 41.725 μl |

Reaction Condition

A vessel containing the reaction solution having the above-mentioned composition was set in the PERKIN ELMER-GeneAmp PCR System 2400 and heated to 97° C. (2 min). Then a cycle of 97° C. (0.25 min)–55° C. (0.5 min)–72° C. (1.5 min) was repeated 10 times, a cycle of 97° C. (0.25 min)–55° C. (0.5 min)–72° C. (2.5 min) was repeated 20 times, and the vessel was kept at 72° C. for 7 min.

To the PCR amplified DNA fragment that had been obtained by the purificarion of the PCR reaction solution were added two kinds of restriction endonucleases (NcoI and BamHI) to double digest the DNA fragment. The obtained DNA fragment was then purified.

On the other hand, two kinds of restriction endonucleases (NcoI and BamHI) were added to the vector pTrc99A (manufactured by Pharmacia Corporation) to double digest the vector. The digested DNA fragment was then purified.

The thus-obtained two DNA fragments were mixed and ligated with T4 DNA ligase. *E. coli* DH5α was transformed with the obtained ligation solution. A vector comprising a wild-type reductase gene (hereinafter also referred to as vector pTrcRPc) was taken from the obtained transformant using QIAprep Spin Miniprep Kit (manufactured by Qiagen Genomics, Inc.)

Example 2

Preparation of a gene of a coenzyme-regenerating gene
(2-1) Preparation for the preparation of a gene having a nucleotide sequence that encodes an amino acid sequence of an enzyme capable of converting an oxydation-type β-nicotineamide adenine dinucleotide etc. into reduction-type An LB medium (1% trypton, 0.5% yeast extract, 1% sodium chloride) (100 ml) was put into a 500 ml flask and sterilized at 121° C. for 15 min. The thus-prepared medium was inoculated with a cultivation solution of *Bacillus megaterium* IF012108 strain that had been previously cultivated in a liquid medium having the above-mentioned composition (30° C., 48 hr, cultivated with shaking) (0.3 ml), and cultivated at 30° C. for 10 hr with shaking.

After cultivation, the obtained cultivation solution was centrifuged (8000×g, 10 min, 4° C.) to collect bacterial cells as precipitate. The collected bacterial cells were washed three times with 50 mM phosphate monopotassium-phosphate dipotassium buffer (pH 7.0) (30 ml) to give wet bacterial cells (about 0.4 g).

A chromosome DNA was purified from the thus-obtained wet bacterial cells using Qiagen Genomic Tip (manufactured by Qiagen Genomics, Inc.) according to the method described in a manual attached thereto.

(2-2) Preparation of a Gene having a Nucleotide Sequence that Encodes an Amino Acid Sequence of an Enzyme Capable of Converting an Oxydation-type β-nicotineamide Adenine Dinucleotide etc. into Reduction-type (Construction of Vector pTrcGDH12)

An oligonucleotide having the nucleotide sequence of SEQ ID NO:8 (including NcoI) and an oligonucleotide having the nucleotide sequence of SEQ ID NO:9 (including BamHI) are synthesized based on the amino acid sequence of the glucose dehydrogenase derived from the known *Bacillus megaterium* IWG3 described in the Journal of Biological Chemistry Vol. 264, No. 11, 6381–6385 (1989).

PCR is carried out using the oligonucleotide having the nucleotide sequence of SEQ ID NO:8 (including NcoI) and oligonucleotide having the nucleotide sequence of SEQ ID NO:9 (including BamHI) as primers, and using the chromosome DNA purified in the above-mentioned (2-1) as a template, at the composition of the reaction solution and reaction condition described in the Example 1 (1-2) (using Expand High Fidelity PCR system, manufactured by Roche Diagnostic Systems Inc.)

To the PCR amplified DNA fragment, which has been obtained by purification of the PCR reaction solution, are added two kinds of restriction endonucleases (NcoI and BamHI) to double digest the DNA fragment. The obtained DNA fragment is then purified.

On the other hand, two kinds of restriction endonucleases (NcoI and BamHI) are added to the vector pTrc99A (manufactured by Pharmacia Corporation) to double digest the DNA fragment. The digested DNA fragment is then purified.

The thus-obtained two DNA fragments are mixed and ligated with T4 DNA ligase. *E. coli* HB101 strain is transformed with the obtained ligation solution. A vector comprising a gene having a nucleotide sequence that encodes an amino acid sequence of an enzyme capable of converting an oxydation-type β-nicotineamide adeninedinucleotide etc. into reduction-type (hereinafter also referred to as vector pTrcGDH12) is taken from the obtained transformant using QIAprep Spin Miniprep Kit (manufactured by Qiagen Genomics, Inc.)

Example 3

Preparation of the Gene of the Present Invention: Introduction of Site-Specific Mutagenesis (3-1) Operation for Introduction of Site-specific Mutagenesis Based on the nucleotide sequence of SEQ ID NO:2, various synthetic oligonucleotides (mutation primers) that correspond to each amino acids were synthesized as mutation primers for converting the amino acids of the positions 54, 104, 245 and 271 into the other amino acids, as represented in SEQ ID NOs: 5, 7, and 10 to 27.

PCR was carried out using an oligonucleotides having the nucleotide sequences of SEQ ID NOs: 5, 7, and 10 to 27 and an oligonucleotide having the nucleotide sequence of SEQ ID NO:6 as primers, and using the vector pTrcRPc purified in the above-mentioned (1-2) as a template, at the following composition of the reaction solution and reaction condition (using Expand High Fidelity PCR system, manufactured by Roche Diagnostic Systems Inc.) The obtained PCR reaction solution is referred to as PCR reaction solution (A). Furthermore, PCR was carried out using an oligonucleotide having the nucleotide sequences of SEQ ID NO:28 and an oligonucleotide having the nucleotide sequence of SEQ ID NO:29 as primers, and using the vector pTrcRPc purified in the above-mentioned (1-2) as a template, at the following composition of the reaction solution and reaction condition (using Expand High Fidelity PCR system, manufactured by Roche Diagnostic Systems Inc.) The obtained PCR reaction solution is referred to as PCR reaction solution (B).

Composition of the Reaction Solution

| | |
|---|---|
| pTrcRPc vector solution | 1 μl |
| dNTP (each 2.5 mM-mix) | 0.4 μl |
| Primer (20 pmol/μl) | Each 0.75 μl |
| 10x buffer (with MgCl$_2$) | 5 μl |
| enz. expand HiFi (3.5 × 10$^3$ U/ml) | 0.375 μl |
| Ultrapure water | 41.725 μl |

PCR Reaction Condition

A vessel containing the reaction solution having the above-mentioned composition was set in the PERKIN ELMER-GeneAmp PCR System 2400. A cycle of 94° C. (0.5 min)-55° C. (2 min)-72° C. (1.5 min) was repeated 25 times and the vessel was kept at 4° C.

The PCR reaction solution (A) and PCR reaction solution (B) were purified respectively, and the resulting two PCR amplified DNA fragments were mixed and heat-denaturated. After the denaturation, they were gradually cooled and annealed. To the fragments were added expand HiFi to complete a heteroduplex, and an oligonucleotide having the nucleotide sequence of SEQ ID NO:28 and an oligonucleotide having the nucleotide sequence of SEQ ID NO:6 were added thereto as primers. PCR was carried out at the following reaction condition (using Expand High Fidelity PCR system, manufactured by Roche Diagnostic Systems Inc.)

PCR Reaction Condition

A vessel containing the reaction solution having the above-mentioned composition was set in the PERKIN ELMER-GeneAmp PCR System 2400. A cycle of 94° C. (0.5 min)-55° C. (2 min)-72° C. (1.5 min) was repeated 10 times and the vessel was kept at 4° C.

The PCR reaction solution was purified and two kinds of restriction endonucleases (NcoI and PstI) were added thereto to double digest the PCR amplified fragment. The digested DNA fragment was then purified.

On the other hand, two kinds of restriction endonucleases (NcoI and PstI) were added to the vector pTrc99A to double digest the vector. The digested DNA fragment was then purified.

The thus-obtained two DNA fragments were mixed and ligated with T4 DNA ligase. *E. coli* HB101 strain was transformed with the obtained ligation solution.

(3-2) Screening of Mutant

A vector was extracted from the transformant obtained in the (3-1), and the nucleotide sequence of the mutated site was determined by dideoxy method to confirm that the designed mutation had been introduced. The operations of the above-mentioned (3-1) and (3-2) were similarly conducted for mutants in which the 17 kinds of leucine of the position 54, the arginine of the position 104, the lysine of the position 245 and asparagine of the position 271 had been replaced, respectively, to give transformants of each mutant plasmids (vectors of the present invention, pL54Q, pL54G, pL54S, pL54T, pL54C, pL54Y, pL54N, pL54A, pL54V, pL54I, pL54M, pL54P, pL54K, pL54R, pL54H, pL54D, pL54E, pR104C, pN271D, pK245R).

Example 4

Preparation of a Multiply-mutated Gene of the Present Invention (4-1) Operation for Introduction of Site-Specific Mutagenesis PCR was carried out using oligonucleotides having the nucleotide sequences of SEQ ID NOs:7, 10 and 11 and an oligonucleotide having the nucleotide sequence of SEQ ID NO:6 as primers, and using the vector purified in the above-mentioned (3-2) (pL54Q) as a template, at the following composition of the reaction solution and reaction condition (using Expand High Fidelity PCR system, manufactured by Roche Diagnostic Systems Inc.) The obtained PCR reaction solution is referred to as PCR reaction solution (C).

Furthermore, PCR was carried out using an oligonucleotide having the nucleotide sequence of SEQ ID NO:28 and an oligonucleotide having the nucleotide sequence of SEQ ID NO:29 as primers, and using the vector purified in the above-mentioned (3-2) (pL54Q) as a template, at the following composition of the reaction solution and reaction condition (using Expand High Fidelity PCR system, manufactured by Roche Diagnostic Systems Inc.) The obtained PCR reaction solution is referred to as PCR reaction solution (D).

Composition of the Reaction Solution

| | |
|---|---|
| Template vector solution | 1 μl |
| dNTP (each 2.5 mM-mix) | 0.4 μl |
| Primer (20 pmol/μl) | Each 0.75 μl |
| 10x buffer (with MgCl$_2$) | 5 μl |
| enz. expand HiFi (3.5 × 10$^3$ U/ml) | 0.375 μl |
| Ultra-pure water | 41.725 μl |

PCR Reaction Condition

A vessel containing the reaction solution having the above-mentioned composition was set in the PERKIN ELMER-GeneAmp PCR System 2400. A cycle of 94° C. (0.5 min)-55° C. (2 min)-72° C. (1.5 min) was repeated 25 times and the vessel was kept at 4° C.

The PCR reaction solution (C) and PCR reaction solution (D) were purified respectively, and the resulting two PCR amplified DNA fragments were mixed and heat-denaturated. After the denaturation, they were gradually cooled and annealed. To the fragments were added expand HiFi to complete a heteroduplex, and an oligonucleotide having the nucleotide sequence of SEQ ID NO:28 and an oligonucleotide having the nucleotide sequence of SEQ ID NO:6 were added thereto as primers. PCR was carried out at the following reaction condition (using Expand High Fidelity PCR system, manufactured by Roche Diagnostic Systems Inc.)

PCR Reaction Condition

A vessel containing the reaction solution having the above-mentioned composition was set in the PERKIN ELMER-GeneAmp PCR System 2400. A cycle of 94° C. (0.5 min)-55° C. (2 min)-72° C. (1.5 min) was repeated 10 times and the vessel was kept at 4° C.

The PCR reaction solution was purified and two kinds of restriction endonucleases (NcoI and PstI) were added thereto to double digest the PCR amplified fragment. The digested DNA fragment was then purified.

On the other hand, two kinds of restriction endonucleases (NcoI and PstI) were added to the vector pTrc99A to double digest the vector. The digested DNA fragment was then purified.

The thus-obtained two DNA fragments were mixed and ligated with T4 DNA ligase. *E. coli* HB11 strain was transformed with the obtained ligation solution.

(4-2) Screening of Mutant

A vector was extracted from the transformant obtained in the (4-1), and the nucleotide sequence of the mutated site was determined by dideoxy method to confirm that the designed mutation had been introduced. By conducting the operations of the above-mentioned (4-1) and (4-2) similarly for the mutants, in each of which the arginine of the position 104, the lysine of the position 245 and the asparagine of the position 271 has been replaced, respectively, the transformants of multiply-mutated vectors (multiply-mutated vectors of the present invention, pL54QR104C, pL54QK245R, pL54QN271D) was obtained. Furthermore, the operations of the above-mentioned (4-1) and (4-2) were similarly conducted for the mutant in which the aspargine of the position 271 has been replaced, using pL54QR104C and pL54QK245R as template vectors, to obtain the transformants of the multiply-mutated vectors (multiply-mutated vectors of the present invention, pL54QR104CN271D, pL54QK245RN271D). In addition, by conducting the operations of the above-mentioned (4-1) and (4-2) similarly for the mutant in which the arginine of the position 104 has been replaced, using pL54QK245RN271D as a template vector, the transformant of the multiply-mutated vector (multiply-mutated vector of the present invention, pL54QR104CK245RN271D) was obtained.

Example 5

Preparation of a Transformant Comprising the Gene of the Present Invention and a Gene of a Coenzyme-regenerating Enzyme Based on the nucleotide sequence of SEQ ID NO:2 (a nucleotide sequence of a gene of a wild-type reductase), an oligonucleotide having the nucleotide sequence of SEQ ID NO:30 (including BamHI) and an oligonucleotide having the nucleotide sequence of SEQ ID NO:31 (including XbaI) were synthesized.

PCR was carried out using the oligonucleotide having the nucleotide sequence of SEQ ID NO:30 (including BamHI) and oligonucleotide having the nucleotide sequence of SEQ ID NO:31 (including XbaI) as primers, and using the vector DNA comprising the wild-type gene or a mutated reductase gene purified in the above-mentioned (1-2), (3-2) or (4-2) as a template respectively, in the following composition of the reaction solution and reaction condition (using the Expand High Fidelity PCR system, manufactured by Roche Diagnostic Systems Inc.)

Composition of the Reaction Solution:

| Vector solution | 1 µl |
| dNTP (each 2.5 mM-mix) | 0.4 µl |
| Primer (20 pmol/µl) | Each 0.75 µl |
| 10x buffer (with MgCl$_2$) | 5 µl |
| enz. expand HiFi (3.5 × 10$^3$ U/ml) | 0.375 µl |
| Ultrapure water | 41.725 µl |

PCR Reaction Condition

A vessel containing the reaction solution having the above-mentioned composition was set in the PERKIN ELMER-GeneAmp PCR System 2400 and heated to 97° C. (2 min). Then a cycle of 97° C. (0.25 min)-55° C. (0.5 min)-72° C. (1.5 min) was repeated 10 times, a cycle of 97° C. (0.25 min)-55° C. (0.5 min)-72° C. (2.5 min) was repeated 20 times, and the vessel was kept at 72° C. for 7 min.

To a PCR amplified DNA fragment obtained by purifying the PCR reaction solution were added two kinds of restriction endonucleases (BamHI and XbaI) to double digest the DNA fragments. The obtained DNA fragments were then purified.

On the other hand, two kinds of restriction endonucleases (BamHI and XbaI) were added to the pTrcGDH12 vector DNA to double digest the vector. The digested DNA fragments were then purified.

The thus-obtained two DNA fragments were mixed and ligated with T4 DNA ligase. *E. coli* DH5a was transformed with the obtained ligation solution. A vector comprising a wild-type reductase gene or a mutated reductase gene (hereinafter also referred to as vectors pTrcGRPc, pTrcGRL54Q, pTrcGRL54G, pTrcGRL54S, pTrcGL54T, pTrcGRL54C, pTrcGRL54Y, pTrcGRL54N, pTrcGRL54A, pTrcGRL54V, pTrcGRL54I, pTrcGRL54M, pTrcGRL54P, pTrcGRL54K, pTrcGRL54R, pTrcGRL54H, pTrcGRL54D, pTrcGRL54E, pTrcGRR104C, pTrcGN271D, pTrcGRK245R, pTrcGRL54QR104C, pTrcGRL54QK245R, pTrcGRL54QN271D, pTrcGRL54QR104CN271D, pTrcGRL54QK245RN271D, pTrcGRL54QR104CK245RN271D) was taken from the obtained transformant using a QIAprep Spin Miniprep Kit (manufactured by Qiagen Genomics, Inc.)

Example 6

Optical Selectivity of the Reductase of the Present Invention

Each of the three transformant obtained in Example 3 or 4 was inoculated in a sterilized LB culture (100 ml) containing IPTG (0.1 mM) and ampicillin (50 µg/ml), and cultivated with shaking at 30° C. for 12 hr. After the cultivation, the obtained cultivation solution was centrifuged (8000×g, 10 min) to collect wet bacterial cells as precipitate. About 0.4 g of wet bacterial cells were obtained.

Methyl 4-bromo-3-oxobutyrate (50 mg), the above-mentioned wet bacterial cells (20 mg), NADP$^+$ (2.4 mg), glucose (100 mg), glucose dehydrogenase (manufactured by Amano Pharmaceuticals, Co., Ltd.) (0.5 mg), 100 mM phosphate buffer (pH 6.5) (2 ml) and butyl acetate (2 ml) were mixed. The mixture was stirred at 30° C. for 20 min. The reaction solution was centrifuged (1000×g, 5 min) to collect the organic layer. The organic layer was subjected to an analysis for optical purity using gas chromatography under the following condition.

Condition for Determination of Optical Purity

Column: G-TA (0.25 mm×30 m, 0.125 µm) (manufactured by Astech, Co., Ltd.)

Column temperature: 110° C. (20 min)→5° C./min →180° C. (1 min)

Carrier gas: helium (flow rate: 1 ml/min)

Detector: FID

Split ratio: 1/50

The absolute configuration of the reaction product was determined by comparing with the sample of methyl (S)-4-bromo-3-hydroxybutyrate.

The results of the analysis for optical purity are shown in Tables 1 and 2.

TABLE 1

| Reductase of the present invention | Optical selectivity (% e.e.) |
|---|---|
| L54Q | 98.7 |
| R104C | 97.7 |
| L54QR104C | 99.0 |
| N271D | 96.8 |
| L54QN271D | 98.6 |
| L54QR104CN271D | 98.8 |
| K245R | 97.0 |
| L54QK245R | 98.6 |
| L54QK245RN271D | 98.3 |
| L54QR104CK245RN271D | 98.7 |
| Wild type reductase (comparative control) | 97.1 |

TABLE 2

| Reductase of the present invention | Optical selectivity (% e.e.) |
|---|---|
| L54Q | 98.7 |
| L54G | 98.3 |
| L54S | 98.8 |
| L54T | 97.7 |
| L54C | 97.5 |
| L54Y | 98.4 |
| L54N | 98.3 |
| L54A | 98.7 |
| L54V | 98.8 |
| L54I | 98.6 |
| L54M | 98.2 |
| L54P | 97.4 |
| L54K | 98.1 |
| L54R | 98.6 |
| L54H | 97.4 |
| L54D | 98.4 |
| L54E | 98.9 |
| Wild type reductase (comparative control) | 97.1 |

As used herein, for example, the "L54Q" in the Tables 1 and 2 represents the reductase of the present invention in which the leucine (L) at the position 54 has been replaced with glutamine (Q), and for example, the "L54QR104C" represents the reductase of the present invention in which the leucine (L) at the position 54 has been replaced with glutamine (Q) and the arginine (R) at the position 104 has been replaced with cysteine (C).

Example 7

Preparation of the Transformant of the Present Invention and Reduction Reaction (Part 1)

*E. coli* HB101 was transformed using the vector pL54Q. The obtained transformant was inoculated in a sterilized LB culture (100 ml) containing IPTG (0.1 mM) and ampicillin (50 µg/ml), and cultivated with shaking at 30° C. for 12 hr. After the cultivation, the obtained cultivation solution was centrifuged (8000×g, 10 min) to collect wet bacterial cells as precipitate. The wet bacterial cells (about 0.4 g) were obtained.

Methyl 4-bromo-3-oxobutyrate (300 mg), the above-mentioned wet bacterial cells (0.4 g), NADP$^+$ (9 mg), glucose (750 mg), glucose dehydrogenase (manufactured by Amano Pharmaceuticals, Co., Ltd.) (1.2 mg), 100 mM phosphate buffer (pH 6.5) (15 ml) and butyl acetate (15 ml) were mixed. The mixture was stirred at 30° C. for 7 hr. During the stirring, 2M aqueous sodium carbonate solution was gradually added to adjust the pH of the reaction solution to 6.5±0.2. After the stirring had been finished, the reaction solution was centrifuged (1000×g, 5 min) to collect the organic layer. The organic layer was subjected to an analysis for content using gas chromatography under the following condition. Methyl 4-bromo-3-hydroxybutyrate was produced 98.5% to the amount of the methyl 4-bromo-3-oxobutyrate used in the reaction. Furthermore, the optical purity of methyl 4-bromo-3-hydroxybutyrate in the organic layer was measured at the following condition, which resulted in 99% e.e. of (S)-form. The organic layer was concentrated to give crude methyl (S)-4-bromo-3-hydroxybutyrate.

Condition for Analysis of Content

Column: HR-20M (0.53 mm×30 m, 1 µm) (manufactured by Shinwa Kako Co., Ltd.)

Column temperature: 120° C. (5 min)→3° C./min→150° C. (5 min)→10° C./min→200° C. (5 min)

Carrier gas: helium (flow rate: 20 ml/min)

Detector: FID

Condition for Determination of Optical Purity

Column: G-TA (0.25 mm×30 m, 0.125 µm) (manufactured by Astech, Co., Ltd.)

Column temperature: 110° C. (20 min)→5° C./min→180° C. (1 min)

Carrier gas: helium (flow rate: 1 ml/min)

Detector: FID

Split ratio: 1/50

The absolute configuration of the reaction product was determined by comparing with the sample of methyl (S)-4-bromo-3-hydroxybutyrate.

Example 8

Preparation of the Transformant of the Present invention and reduction reaction (Part 2)

*E. coli* HB101 was transformed using the vector pTrcGRL54Q. The obtained transformant was inoculated in a sterilized LB medium (100 ml) containing IPTG (0.1 mM) and ampicillin (50 μg/ml), and cultivated with shaking at 30° C. for 12 hr. About 0.4 g of wet bacterial cells were obtained.

Methyl 4-bromo-3-oxobutyrate (300 mg), the above-mentioned wet bacterial cells (0.4 g), NADP$^+$ (9 mg), glucose (750 mg), 100 mM phosphate buffer (pH 6.5) (15 ml) and butyl acetate (15 ml) were mixed. The mixture was stirred at 30° C. for 7 hr. During the stirring, 2M aqueous sodium carbonate solution was gradually added to adjust the pH of the reaction solution to 6.5±0.2. After the stirring had been finished, the reaction solution was centrifuged (1000×g, 5 min) to collect the organic layer. The organic layer was subjected to an analysis for content using gas chromatography under the following condition. Methyl 4-bromo-3-hydroxybutyrate was produced 98.5% to the amount of the methyl 4-bromo-3-oxobutyrate used in the reaction. Furthermore, the optical purity of methyl 4-bromo-3-hydroxybutyrate in the organic layer was measured at the following condition, which resulted in 99% e.e. of (S)-form. The organic layer was concentrated to give crude methyl (S)-4-bromo-3-hydroxybutyrate.

Condition for Analysis of Content

Column: HR-20M (0.53 mm×30 m, 1 μm) (manufactured by Shinwa Kako Co., Ltd.)

Column temperature: 120° C. (5 min)→3° C./min→150° C. (5 min)→10C/min→200° C. (5 min)

Carrier gas: helium (flow rate: 20 ml/min)

Detector: FID

Condition for Determination of Optical Purity

Column: G-TA (0.25 mm×30 m, 0.125 μm) (manufactured by Astech, Co., Ltd.)

Column temperature: 110° C. (20 min)→5° C./min→180° C. (1 min)

Carrier gas: helium (flow rate: 1 ml/min)

Detector: FID

Split ratio: 1/50

The absolute configuration of the reaction product was determined by comparing with the sample of methyl (S)-4-bromo-3-hydroxybutyrate.

Example 9

Production of the Reductase of the Present Invention Using Transformants

The 26 transformants obtained in Example 3 or 4 were inoculated in an LB medium (50 ml) containing IPTG (0.1 mM) and ampicillin (100 μg/ml), and cultivated with shaking at 30° C. for 12 hr. After the cultivation, the obtained cultivation solution was centrifuged (8000×g, 10 min) to collect bacterial cells as precipitate. A part of the collected bacterial cells (corresponding to 5 μl of the cultivated solution) were subjected to SDS-PAGE. For all of the 26 samples, a protein was observed as a major band at the position corresponding to the molecular weight of the wild-type reductase.

Example 10

Purification of the Reductase of the Present Invention

Each of the 26 transformants cultivated according to the method of Example 9 is crushed by ultrasonic (20 KHz, 15 min, 4° C.) and centrifuged (100000×g, 60 min, 4° C.) to give supernatant. To the obtained ultracentrifuged supernatant (150 ml) is added ammonium sulfate until its concentration reaches to 1.5 M. The solution is spread on a hydrophobic interaction chromatography column [Hi-Load Phenyl (26/10) (manufactured by Amersham Pharmacia Biotech, Inc.)] [equilibrated with BIS-TRIS-PROPANE buffer containing 1.5 M ammonium sulfate (20 mM, pH 7.0)], and the objective enzyme is eluted using BIS-TRIS-PROPANE buffer including ammonium sulfate (having concentration gradient of ammonium sulfate of 1.5 M→0.6 M) as a mobile phase. The determination of the activity of the enzyme for the eluted fraction is carried out using 4-halo-3-oxobutyrate ester, which is a substrate for reductase.

Specifically, a phosphate buffer including methyl 4-bromo-3-oxobutyrate (1.56 mg/ml) and NADPH (0.226 mg/ml) (20 mM, pH 7.0, 0.9 ml) is added to the eluant including the eluted fraction (0.1 ml), and the mixture is kept at 30° C., and the increase of the absorbance at 340 nm is measured. The fraction having the activity of the reductase is collected, desalted and replaced with Tris-HCl buffer (20 mM, pH 7.7). The fraction is spread on an ion exchange chromatography column [Hi-Load Q Sepharose (16/10) (manufactured by Amersham Pharmacia Biotech, Inc.)] [equilibrated with Tris-HCl buffer (20 mM, pH 7.7)], and the objective enzyme is eluted using Tris-HCl buffer including sodium chloride (having concentration gradient of sodium chloride of 0→0.5 M) as a mobile phase. The fraction having the activity of the reductase is collected to give the purified reductase.

According to the present invention, there is provided a reductase, which is used for an organic synthesis reaction for production of compounds used as active ingredients of medicaments or agrochemicals or intermediates thereof, especially optically active compounds or intermediates thereof and the like, and is good at the production of reaction products having good optical purity.

What is claimed is:

1. An isolated βketo acid reductase comprising the amino acid sequence of SEQ ID NO:1 except that:
   (a) the amino acid at amino acid position 54 is substituted with glutamine, glycine, serine, threonine, cysteine, asparagine, alanine valine, isoleucine, methionine, lysine, arginine, aspartic acid, glutamic acid, tyrosine, proline or histidine;
   the amino acid at amino acid position 245 is substituted with arginine or another amino acid; and
   the amino acid at position 271 is substituted with asparagine or another acid;
   (b) the amino acid at amino acid position 104 is substituted with cysteine;
   the amino acid at amino acid position 245 is substituted with arginine or another amino acid; and
   the amino acid at position 271 is substituted with asparagine or another acid; or
   (c) the amino acid at amino acid position 54 is substituted with glutamine, glycine, serine, threonine, cysteine, asparagine, alanine valine, isoleucine, methionine, lysine, arginine, aspartic acid, glutamic acid, tyrosine, proline or histidine;
   the amino acid at amino acid position 104 is substituted with cysteine;
   the amino acid at amino acid position 245 is substituted with arginine or another amino acid; and
   the amino acid at position 271 is substituted with asparagine or another acid.

2. The reductase according to claim 1, wherein the amino acid at position 245 is substituted with arginine.

3. The reductase according to claim 1, wherein the amino acid at position 271 is substituted with aspartic acid.

4. The reductase according to claim 1, wherein
   (a) the amino acid at amino acid position 54 is substituted with glutamine and the amino acid at amino acid position 104 is substituted with cysteine;
   (b) the amino acid at amino acid position 54 is substituted with glutamine, the amino acid at amino acid position 104 is substituted with cysteine and the amino acid at amino acid position 271 is substituted with aspartic acid;
   (c) the amino acid at amino acid position 54 is substituted with glutamine, the amino acid at amino acid position 104 is substituted with cysteine, the amino acid at amino acid position 245 is substituted with arginine and the amino acid at amino acid position 271 is substituted with aspartic acid;
   (d) the amino acid at amino acid position 54 is substituted with glutamine and the amino acid at amino acid position 245 is substituted with arginine;
   (e) the amino acid at amino acid position 54 is substituted with glutamine, the amino acid at amino acid position 245 is substituted with arginine and the amino acid at amino acid position 271 is substituted with aspartic acid; or
   (f) the amino acid at amino acid position 54 is substituted with glutamine and the amino acid at amino acid position 271 is substituted with aspartic acid.

5. A method for modifying a βketo acid reductase, which consists of substituting one of the amino acid at positions 54 or 104 of the amino acid sequence of SEQ ID NO:1 with another amino acid or substituting both the amino acids at amino acid positions 54 and 104 of the amino acid sequence of SEQ ID NO:1 with another amino acid, wherein
   the amino acid at amino acid position 54 is substituted with glutamine, glycine, serine, threonine, cysteine, asparagine, alanine valine, isoleucine, methionine, lysine, arginine, aspartic acid, glutamic acid, tyrosine, proline or histidine; and
   the amino acid at amino acid position 104 is substituted with cysteine; and wherein the modified β-keto acid reductase continues to have β-keto acid reductase activity.

* * * * *